US008187857B2

(12) United States Patent
Robinson

(10) Patent No.: US 8,187,857 B2
(45) Date of Patent: May 29, 2012

(54) MULTICELLULAR ORGANISMS DERIVED FROM NORMAL/NONDISEASED AND DISEASED MAMMALIAN TISSUES

(75) Inventor: Douglas H. Robinson, Washington, DC (US)

(73) Assignee: Denovo Biologic LLC, Arlington, VA (US)

( * ) Notice: Subject to any disclaimer, the term of this patent is extended or adjusted under 35 U.S.C. 154(b) by 1037 days.

(21) Appl. No.: 10/593,800

(22) PCT Filed: Mar. 17, 2005

(86) PCT No.: PCT/US2005/008920
§ 371 (c)(1),
(2), (4) Date: Mar. 8, 2007

(87) PCT Pub. No.: WO2005/090554
PCT Pub. Date: Sep. 29, 2005

(65) Prior Publication Data
US 2007/0178468 A1    Aug. 2, 2007

Related U.S. Application Data

(60) Provisional application No. 60/554,225, filed on Mar. 17, 2004.

(51) Int. Cl.
*C12N 1/00* (2006.01)
*C12N 1/12* (2006.01)
*C12N 5/00* (2006.01)

(52) U.S. Cl. ........................ 435/243; 435/252.1; 435/325

(58) Field of Classification Search .................. None
See application file for complete search history.

(56) References Cited

FOREIGN PATENT DOCUMENTS
WO    WO 98/13472    4/1998

OTHER PUBLICATIONS

Robinson D.H.: "Pleomorphic mammalian tumor-derived bacteria self-organize as multicellular mammalian eukaryotic-like organisms: morphogenetic properties in vitro, possible origins, and possible roles in mammalian 'tumor ecologies'", Medical Hypotheses, Eden Press, Penrith, US, vol. 64,No. 1, 2005, pp. 177-185 XP004729060, ISSN: 0306-9877.
Wainwright M: "Highly pleomorphic *Staphylococci* as a cause of cancer," Medical Hypotheses. Jan. 2000, vol. 54, No. 1, Jan. 2000, pp. 91-94, XP002335514, ISSN: 0306-9877.
Wainwright, Milton et al.: "Is this the historiaal 'cancer germ'?", Medical Hypotheses, Feb. 2003, vol. 60, No. 2, Feb. 2003, pp. 290-292, XP002335515, ISSN: 0306-9877.
Macomber P B: "Cancer and cell wall deficient bacteria.", Medical Hypotheses, May 1990, vol. 32, No. 1, pp. 1-9, XP008049529, ISSN: 0306-9877.
Backus B T et al.: "Tumor-associated bacteria capable of producing a human choriogonadotropin-like substance.", Infection and Immunity, Jun. 1981, vol. 32, No. 3, pp. 1211-1215, XP002335516, ISSN: 0019-9567.
Robinson D.H.: An oxygen-related bioprocess drives eukaryote-to-prokaryote prokaryote genome evolution and speciation, DeNOVO Biologic LLC, 2001.

*Primary Examiner* — Albert Navarro
(74) *Attorney, Agent, or Firm* — Kenyon & Kenyon LLP

(57) ABSTRACT

The present invention relates to pleomorphic cells ("morphotes"), which exhibit morphologic and genetic characteristics of both prokaryotic and eukaryotic cells, including resemblance to prokaryotic cells at the unicellular level, and resemblance to eukaryotic cells at the multicellular level due to their ability to self-organize in vitro into multicellular, mammalian tissue-like patterns consisting of tissue-like sheets, capillary-like networks, and trabecular (spongy) bone-like structures. Morphotes have a number of applications in the diagnostic medical, therapeutic medical, biological, biomaterials, bio-nanotechnological, and industrial fields.

5 Claims, 10 Drawing Sheets

MULTICELLULAR ORGANISMS DERIVED FROM NORMAL/NONDISEASED AND DISEASED MAMMALIAN TISSUES

This is a 371 national phase application of PCT/US2005/008920 filed 17 Mar. 2005, claiming priority to U.S. Provisional Patent Application No. 60/554,225 filed 17 Mar. 2004, the contents of which are incorporated herein by reference.

TECHNICAL FIELD

The present invention relates to cells and cell cultures, and methods of using the same for therapeutic, diagnostic and surgical purposes, and to produce biomaterial of medical and industrial utility.

BACKGROUND OF THE INVENTION

Multicellularity represents one of the major transitions in the evolution of biologic complexity.[1] Bacterial species such as *Myxococcus xanthus* exhibit characteristics of multicellular organisms, including cooperative behavior among individuals and coordinated cell-cell attachments.[2] Here it is shown that pleomorphic cells derived from mammalian tumor exhibit morphologic and genetic characteristics of both prokaryotic and eukaryotic cells, among the most conspicuous of which is the resemblance to prokaryotic cells at the unicellular level, combined with the ability to self-organize in vitro into multicellular, mammalian eukaryotic tissue-like patterns consisting of tissue-like sheets, capillary-like networks, and trabecular (spongy) bone-like structures. This multicellularity is unlike any previously reported.

SUMMARY OF THE INVENTION

The present invention relates to pleomorphic organisms which exhibit morphologic and genetic characteristics of both prokaryotic and eukaryotic cells, including resemblance to prokaryotic cells at the unicellular level, and the ability to self-organize into multicellular, mammalian eukaryotic tissue-like patterns consisting of tissue-like sheets, capillary-like networks, and trabecular (spongy) bone-like structures. These organisms, as hereinafter further described, are termed "morphotes" by the inventor.

In one preferred embodiment, the morphotes exhibit multicellar self-organization into tissue-like sheets when cultured in vitro.

In another preferred embodiment, the morphotes exhibit multicellular self-organization into capillary-like networks when cultured in vitro.

In another preferred embodiment, the morphotes exhibit multicellular self-organization into trabecular (spongy) bone-like structures.

The morphotes of the present invention can be used to produce in vitro autologous or allogenic therapeutic or prophylactic vaccines for treatment of cancer, AIDS, and other mammalian diseases.

The morphotes of the present invention derived from the tissues of patients with HIV infection and/or AIDS can be used to produce vaccines against HIV infection and/or AIDS.

The morphotes of the present invention derived from normal or aging mammalian tissues can be used to produce vaccines against cellular and tissue degradation due to chronic infection with morphotes, which results in chronic inflammation and the aging process.

The morphotes of the present invention derived from diseased/abnormal mammalian tissues can be used to develop antibiotics and vaccines to eradicate morphotes from such diseased/abnormal mammalian tissues in vivo.

The morphotes of the present invention isolated from apparently healthy individuals can also be used as an in vitro marker for impending disease prior to clinical detection of the disease.

The morphotes of the present invention can be used to produce, in vitro, proteins as markers to diagnose various mammalian diseases and predispositions to disease (pre-disease states) associated with morphote infection.

The morphotes of the present invention can be used to produce morphote-specific antibodies to aid in the diagnosis of various mammalian diseases and predisposition to disease (pre-disease states) associated with morphote infection.

The morphotes of the present invention can be used to produce in vitro DNA, cDNA, and oligonucelotide microarrays or biochips to aid in the diagnosis of morphote infections associated with cancer, AIDS, and other human The morphotes of the present invention can be used to produce morphote-specific antibodies to aid in the diagnosis of morphote infections associated with cancer, AIDS, and other human diseases and pre-disease states.

The morphotes of the present invention can be used to identify eukaryotic genes and proteins involved in mammalian morphogenesis that can be used to treat and/or develop new treatments for various mammalian diseases, such as congenital heart disease and cardiomyopathies, blood vessel abnormalities and atherosclerosis, pulmonary alveolar abnormalities, etc.

The morphotes of the present invention can be used as an in vitro model to test new or existing drugs and biomolecules that disrupt/kill morphotes that are integral to the pathogenesis of mammalian cancer and other mammalian diseases.

The morphotes of the present invention can be used in vitro as a model to test new or existing radiofrequency therapeutic modalities that disrupt/kill morphotes that are integral to the pathogenesis of mammalian cancer and other mammalian diseases.

The morphotes of the present invention, either viable or nonviable, can be used to promote angiogenesis and wound repair in vivo by placing them directly into diseased mammalian tissues or mammalian wounds.

The morphotes of the present invention can be used to express novel genes/proteins, i.e., chimerical (eukaryotic/prokaryotic) proteins or proteins with little homology to known proteins, useful in diagnosing and treating mammalian diseases associated with morphote infection. The morphotes of the present invention also can be used as a cloning vectors to express other genes/proteins of interest in a morphote mesh-like or tissue-like pattern of distribution.

The morphotes of the present invention can be used in vitro to produce growth-promoting proteins or elastic proteins (bioelastomers, elastomeric proteins, or biopolymers), in sheets, tissue-like networks or trabecular (spongy) bone-like structures, to treat mammalian diseases such as ligament injuries/defects or burns, or as a matrix for skin grafting, or to promote host skin growth/repair, heart valve injuries/defects, and other diseases or disorders of bone, connective tissue, etc.

The morphotes of the present invention can be used, either as unmodified isolates or genetically modified, to produce biomolecules (e.g., bioelastomers, elastomeric proteins, biopolymers, etc.), and other polymers such as polyesters, to be used in medical biomaterials science applications such as the in vitro production of implantable cellular scaffold biomaterial for growing mammalian eukaryotic cells and/or tissues for arterial grafts, skin grafts, bone grafts, heart valves, etc.; synthetic ligaments; synthetic suture materials; biosensors; materials for drug delivery; coatings for catheters, etc.

The morphotes of the present invention can be used, either as unmodified isolates or genetically modified, to produce elastic proteins (bioelastomers, elastomeric proteins, or biopolymers), or other proteins and polymers, to be used in industrial materials science applications, such as protective body armor; acoustical absorbers; durable elastic thermoplastics, fibers, etc.

The morphotes of the present invention can be used to produce in vitro bulk industrial/commercial enzymes, e.g., polymer-degrading enzymes, and other proteins of industrial significance to process food substances, make detergents, bate leather, etc. and, especially, for applications were a controlled or discrete site of action is required, such as in waste treatment such as sewerage treatment and chemical or oil spills.

The morphotes of the present invention, either as unmodified isolates or genetically modified, can be used to study the evolution and development of mammalian eukaryotic stem cells and can be used to develop novel genes, proteins, and products for therapeutic and/or diagnostic applications in mammalian eukaryotic stem cell biology and medicine.

DETAILED DESCRIPTION OF THE INVENTION

Figure 1:
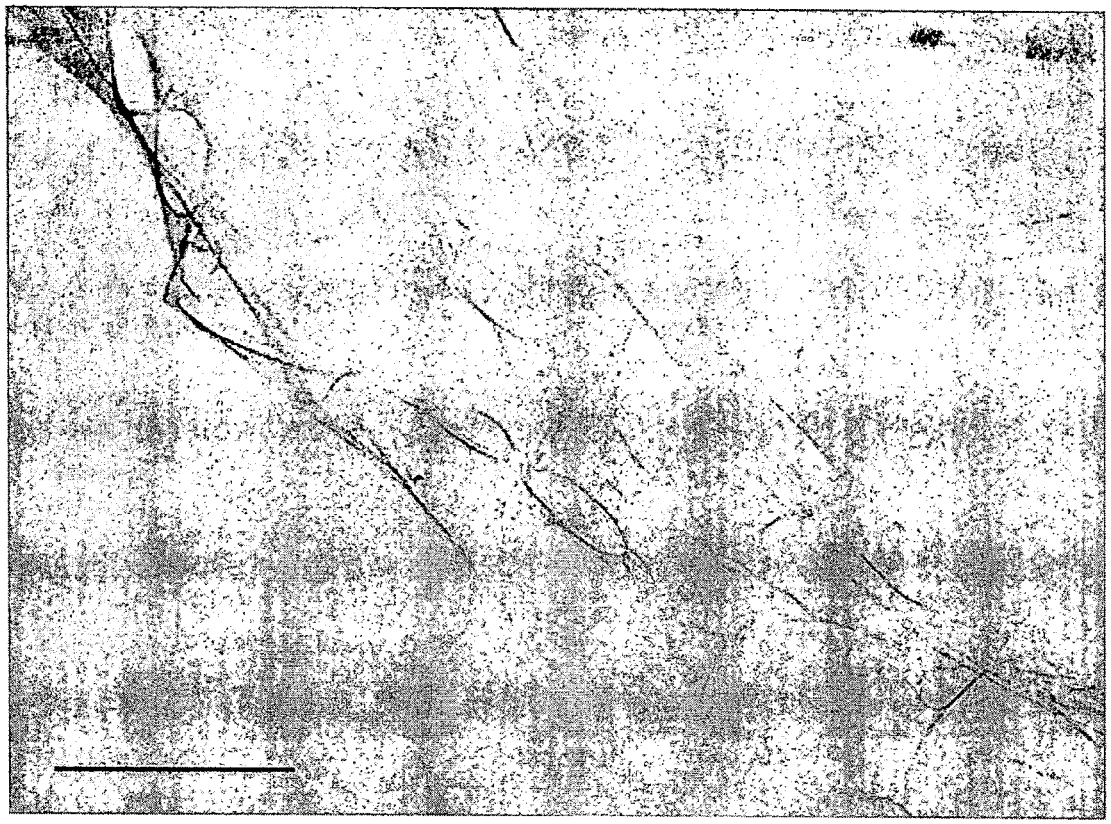
FIG. 1 shows the morphote isolate MH self-organized into multicellular tissue-like sheets that contained numerous lacunae (8-day old liquid culture; stained with the supravital dye new methylene blue N solution (Brecher formula) and examined by light microscopy). Scale bar=500 µm.

The present invention relates to pleomorphic cells, designated "morphotes" by the inventor, which exhibit morphologic and genetic characteristics of both prokaryotic and eukaryotic cells, including resemblance to prokaryotic cells at the unicellular level, and resemblance to eukaryotic cells at the multicellular level due to their ability to self-organize into multicellular, mammalian tissue-like patterns consisting of tissue-like sheets, capillary-like networks, and trabecular (spongy) bone-like structures. In general, multicellularity in morphotes is defined as the cellular connection or interconnection of three or more morphote cells into networks of varying densities, scales, or dimensions that tessellate triangular, quadrilateral, and polygonal areas or shapes that contain no morphote cells.

The multicellular self-organization in vitro of morphotes into tissue-like sheets and capillary-like networks shows some similarities to morphogenetic patterns observed in in vitro models of mammalian vascular network formation.[3,4] However, this multicellular self-organization exhibits an autonomy and complexity of biological pattern formation not observed in these in vitro models of mammalian vascular network formation. Notably, while these models require extracellular matrix (ECM)-coated culture vessels to support endothelial cell self-organization, morphotes can self-organize in vitro in simple tryptic soy broth nonadherently and without the use of exogenous ECM. Other morphogenetic properties of morphotes include the ability to form trabecular (spongy) bone-like structures.[5,6] Indeed, the morphogenetic properties of morphotes, including the ability to develop into tissue-like, capillary-like, and bone-like sheets, networks, and structures, indicates that morphotes possess features attributed to the mammalian eukaryotic mesenchymal stem cell and, therefore, may be considered to be mammalian eukaryotic mesenchymal stem cell-like.[7]

Studies using sequence-based comparative genomics indicate that some bacterial species appear to have acquired a significant number of genes from their eukaryotic hosts through horizontal gene transfer. While not wishing to be bound by theory, it is hypothesized that morphotes express eukaryote-derived genes related to mammalian angiogenesis[8] and, perhaps, other eukaryote-derived genes that were acquired by way of eukaryote-to-prokaryote DNA transfer from eukaryotic tumor cells.

As coevolved partners with animal eukaryotic cells, symbiotic bacteria have been shown to wield significant influence on animal development.[9] In symbiosis with mammalian eukaryotic tumor cells and mammalian capillary endothelial cells, morphotes and similar multicellular tumor-derived organisms would wield significant influence on mammalian tumor development. As symbiotic capillary-like facultative anaerobes, they would stimulate tumor neovascularization, functioning as "roadmaps" that guide mammalian endothelial cell migration into anaerobic regions of the tumor microenvironment; the bacteria *Bartonella henselae* and *Agrobacterium tumefaciens* have been shown to trigger neovascularization in humans and plants, respectively.[10,11] One "ecological" benefit of the interaction of tumor-derived morphotes with mammalian eukaryotic tumor cells and mammalian capillary endothelial cells would be the generation of an optimized morphote habitat in which the morphotes would be assured a nutrient supply and host immune tolerances.[9,10]

Morphotes have a number of applications in the diagnostic medical, therapeutic medical, biological, biomaterials, and industrial fields.

For example, because morphotes appear to be associated with diseased mammalian tissues (e.g., cancer and viral infection), they can be used to produce in vitro autologous or allogenic therapeutic or prophylactic vaccines for treatment of mammalian cancer, AIDS, and other diseases. Without being bound by theory, it is believed that morphotes play an integral role in the causation, progression, and/or maintenance of at least some types of mammalian disease states.

Morphotes derived from mammalian cancer cells of a specific type, such as lymphoma, melanoma, leukemia, or hormone-dependant cancers such as breast and prostate cancers, can be used, in either attenuated (live) or killed form, as suitable, cell-specific vaccines against such cancers, by inhibiting or eradicating morphotes associated with such cancers in vivo. Likewise, morphote-based vaccines made using morphotes isolated from mammalian cells infected with a pathogen, such as HIV, HSV, hepatitis, etc., can be used as preventative or therapeutic vaccines against such pathogens or pathogenic diseases.

Chronic bacterial infection and chronic inflammation appear to be significant factors in human aging.[12] There also is mounting evidence that at least some aspects of the "natural" mammalian aging process involve chronic increased levels of inflammatory mediators and programmed cell death.[13,14] It is possible that the presence of morphotes in mammalian tissues is a contributing, or even a causative, factor in aging-related chronic inflammatory states, generated, in part, by a mammalian immune system that works to eliminate chronic localized or systemic morphote infection. Inhibition or eradication of the causative morphotes would retard or prevent aging-related cellular and tissue damage due to chronic morphote infection. Thus, morphotes of the present invention derived from normal or aging mammalian tissues can be used to produce vaccines and/or therapeutic agents against the aging-related cellular and tissue degradation associated with morphote infection.

Another application for the morphotes of the present invention is as a marker for diagnosis of disease and predispositions to disease (pre-disease states). In the case of pre-disease states, infection with morphotes, which by definition is typically subclinical, may precede the development of clinical disease. Therefore, detection and eradication of subclinical morphote infection associated with a subclinical disease process can help reverse the disease process prior to its clinical expression or retard progression of the disease process in the event that it is expressed clinically. Morphotes derived from mammalian cells exhibiting particular disease states can be used to produce, in vitro, proteins as markers to diagnose various mammalian diseases and pre-disease states associated with morphote infection. Alternatively, morphote proteins can be used to develop morphote-specific antibodies to aid in the diagnosis of various mammalian diseases and pre-disease states associated with morphote infection.

Similarly, using recent hybrid diagnostic technologies (for example, that disclosed in U.S. Pat. No. 6,228,575), morphotes can be used to produce in vitro DNA, cDNA, and oligonucleotide microarrays or biochips to aid in the diagnosis of disease and pre-disease states associated with cancer, AIDS, and other mammalian diseases.

The morphotes of the present invention also can be used as an in vitro model to screen new or existing drugs and biomolecules that disrupt/kill morphotes that are integral to the pathogenesis of mammalian cancer and other mammalian diseases. A method for screening drugs for efficacy against mammalian disease states would comprise (a) exposing a culture of morphotes, derived from diseased mammalian tissues, and exhibiting multicellular self-organization when cultured in vitro, to a candidate drug or biomolecule, and (b) culturing said morphotes in the presence of the candidate drug or biomolecule for a time sufficient to determine whether said morphotes are inhibited or killed by said candidate drug or biomolecule, inhibition or killing being an indicator of therapeutic efficacy of the drug. Similarly, the molphotes of the present invention be used in vitro as a model to test new or existing radiofrequency, radiological, and other non-drug therapeutic modalities that disrupt/kill morphotes that are integral to the pathogenesis of mammalian cancer and other mammalian diseases.

The morphotes of the present invention, either viable or nonviable, can be used to promote angiogenesis and wound repair in vivo by placing them directly into mammalian wounds. For example, self-organized meshes of morphotes, which may contain and express various growth factors (mammalian eukaryote-derived and others), may be treated so as to be nonviable, yet continue to harbor active growth factor proteins in or on their cell walls, thus creating, in essence, a mesh of active growth factor proteins. This morphote-derived growth factor mesh can then be applied to mammalian wounds to stimulate wound repair and angiogenesis. Some morphote meshes devised for mammalian wound repair can contain peptidoglycan, a substance which helps stimulate mammalian wound repair.[15]

The morphotes of the present invention can be used to express novel genes/proteins, i.e., chimerical (eukaryotic/prokaryotic) proteins or proteins with little homology to known proteins, for the treatment of various mammalian diseases, including those that are associated with morphote infection. For example, a morphote cell line can express naturally (i.e., without the use of genetic engineering or gene cloning) a novel protein(s) that is useful in the treatment of mammalian cancers, autoimmune diseases, AIDS, bacterial and viral infections, mammalian diseases associated with morphote infection, etc. The uniqueness or novelty of these proteins would correlate with the uniqueness or novelty of morphotes and their unique or novel evolutionary and developmental life history; as such, these proteins would not be found in or expressed by other known life forms. Novel morphote-derived proteins would be isolated from morphotes and developed for the treatment of mammalian cancers, autoimmune diseases, AIDS, bacterial and viral infections, mammalian diseases associated with morphote infection, etc.

The morphotes of the present invention also can be used as cloning vectors to express other genes/proteins of interest in a morphote mesh or tissue-like pattern of distribution. Such genetically engineered morphote meshes could be, in a medical setting, treated so as to be nonviable and, subsequently, applied to mammalian wounds in order to accelerate wound repair, or could be, in an industrial setting, cultured in or on a material to be treated in order to degrade or detoxify toxic substances in that material.

The morphotes of the present invention can be used to produce in vitro novel antibiotics to treat mammalian diseases, including, but not limited to, cancers and infectious diseases. Various species of bacteria produce antibiotics that are used to treat mammalian cancers and infectious diseases. Similarly, morphotes with their bacterial-like features may produce novel antibiotics that can be used to treat mammalian cancers and infectious diseases.

One significant advantage of the present invention is the ability to culture morphotes in a controlled or pre-determined pattern or shape (for example, by restriction of the culture area, or the application of growth promoters or inhibitors, or both, to defined portions of a culture substrate). This allows the formation of a number of materials useful in a variety of medical and industrial applications. Morphotes can be cultured in such a predetermined pattern or shape, and the cellular material removed or made nonviable, for example by mild detergent, to leave a structure of protein or other polymer of a desired shape or pattern for use in the various ways described above, or the living morphotes can be left intact in the developed structure, to further grow and/or produce therapeutic or industrially useful substances after application to a treatment site.

The morphotes of the present invention can be used, either as unmodified isolates or genetically modified, to produce biomolecules (bioelastomers, elastomeric proteins, biopolymers, etc.), and other polymers such as polyesters, to be used in medical biomaterials science applications such as the in vitro production of implantable cellular scaffold biomaterials for growing mammalian eukaryotic cells and/or tissues for arterial grafts, skin grafts, bone grafts, heart valves, etc.; synthetic ligaments; synthetic suture materials; biosensors; materials for drug delivery; coatings for catheters, etc. In the case of in vitro applications, morphotes would be cultured in vitro to form the cellular scaffold biomaterial(s); subsequently, morphotes in the morphote cellular scaffold would be treated so as to be nonviable, leaving behind the cellular scaffold consisting of nonviable biomaterial(s). Mammalian eukaryotic cells would then be cultured on the nonviable morphote cellular scaffold biomaterial(s), assuming its shape(s) during proliferation. The mammalian eukaryotic cell-impregnated morphote cellular scaffold would then be placed in vivo into the living mammalian tissue of interest, where it would exist as a mammalian tissue substitute and would stimulate the growth and repair of surrounding endogenous mammalian tissue. Alternatively, the morphotes would remain viable in the morphote cellular scaffold, prior to culturing mammalian eukaryotic cells on the morphote cellular scaffold, and, subsequently, would be rendered nonviable prior to implantation of the mammalian eukaryotic cell-impregnated morphote cellular scaffold into the mammalian tissue of interest or would be left viable prior to such implantation.

The morphotes of the present invention can be used to produce elastic proteins (bioelastomers, elastomeric proteins, or biopolymers) and other proteins to be used in industrial materials science applications, such as protective body armor; acoustical absorbers; durable elastic thermoplastics, etc. Transformation of morphote cell lines with genes encoding the appropriate synthetic enzymes would enable them to produce such biopolymers (e.g., elastin, see U.S. Pat. No. 5,969,106, or spider silk, see U.S. Pat. Nos. 6,268,169, 5,728, 810), or alternatively organic polymers such as polyester (See, e.g., U.S. Pat. Nos. 5,981,257, 6,479,145, 6,759,219).

The morphotes of the present invention can be used to produce in vitro bulk industrial/commercial enzymes, e.g., polymer-degrading enzymes, and other proteins of industrial significance. Enzymes isolated from bacteria are used in many industrial applications to process food substances, make detergents, bate leather, etc. Bulk industrial enzymes isolated from morphotes may be equal to or superior to existing industrial enzymes in terms of quality and cost effectiveness with regard to a particular industrial/commercial application. Furthermore, the production of industrial/commercial enzymes in a morphote network or mesh-like structure permits their production and/or use in a controlled pattern or three-dimensional structure.

The morphotes of the present invention, either as direct isolates or genetically modified, can be used in sewerage and other waste treatment such as chemical and oil spills, either as an unorganized seed culture applied to the material to be treated, which then multiplies and forms an organized multicellular structure throughout the treated material, or by preforming a matrix for application on or in the material to be treated, similar to the microbial mats described in U.S. Pat. No. 5,614,097. In addition to the treatment function, such organized morphote networks offer the additional benefit of containing, isolating, and controlling the spread of, the waste being treated.

The morphotes of the present invention, either isolated or genetically modified, can be used to study the evolution and development of mammalian eukaryotic stem cells and can be used to develop novel genes, proteins, and products for therapeutic and/or diagnostic applications in mammalian eukaryotic stem cell biology and medicine. For example, because the multicellular mammalian eukaryotic tissue-like patterns of morphote morphogenesis indicate that morphotes may be considered to be mammalian eukaryotic mesenchymal stem cell-like, then various morphote-derived proteins, genes, or other products can be used to study, understand, and manipulate mammalian eukaryotic mesenchymal stem cell evolution and development. Accordingly, morphote-derived proteins, genes, or other products can be used to diagnosis and treat mammalian eukaryotic mesenchymal stem cell-related diseases and disorders or can be used to accelerate the growth and differentiation of mammalian eukaryotic mesenchymal stem cells in vitro for use in vivo in various medical applications.

The following examples are intended to illustrate, but in no way to limit, the invention, the scope of which is defined by the claims.

EXAMPLE 1

Highly pleomorphic bacteria have been regularly isolated from mammalian tumors.[16] To determine if the pleomorphism of mammalian tumor-derived bacteria might be associated with eukaryote-to-prokaryote gene transfer,[17] morphotes from canine lymphoma specimens were first isolated using a culture method that involves subjecting eukaryotic cells to an environmental pressure of alternating anaerobic and aerobic atmospheres[18] as follows:

1. Lymphoma specimens were collected from canines under sterile conditions.
2. Specimens were cut into several pieces with sterile scalpel/scissors in sterile conditions under laminar flow hood.
3. Specimens were placed into 5-8 ml of culture medium (bacteriological or eukaryotic) in sterile vented 60 mm Petri dishes in sterile conditions under laminar flow hood. The Petri dishes were covered.
4. Petri dishes containing specimens and media were placed in an anaerobic jar [Mitsubishi AnaeroPouch™ System Pouch-Rectangular Jar (0.4 L), Order No. 40-04], a gas generating pouch [Mitsubishi AnaeroPouch™ System Pouch-Anaero, Order No. 20-01] was added to the jar, and the jar was sealed to establish an anaerobic atmosphere.
5. The anaerobic jar was transferred to an incubator set at 37° C., and incubated for 24 hours.
6. The anaerobic jar was removed from the incubator, and the Petri dishes were removed from the jar.
7. The Petri dishes were opened and the specimens and media exposed to air for 10-15 minutes in sterile conditions under a laminar flow hood. The Petri dishes were covered.
8. Steps 4-7 were repeated.
9. A final anaerobic culturing cycle was performed as in steps 4 and 5.
10. The anaerobic jar was removed from incubator and the Petri dishes were removed from the jar.

11. All material (specimens and media) was transferred from the Petri dishes into bacteriological media bottles in sterile conditions under laminar flow hood.
12. The sterilely vented bacteriological media bottles were then transferred to an incubator set at 20-25° or 37° C.
13. Bacteriological media bottles were observed daily for signs of turbidity for several weeks. Frequent samples were collected under sterile conditions for examination by light microscopy.
14. When bottles became turbid, bottle contents were streaked onto solid media plates, and the plates were incubated for signs of cell growth using standard conditions.

EXAMPLE 2

After isolation according to the methods of Example 1, and culture on solid media, isolates were analyzed using the automated Dade Behring MicroScan Walkaway® Microbiology System (Dade Behring, Inc., Deerfield, Ill.) for ID/AST (identification/antibiotic sensitivity testing) to determine biochemical profiles and 16S ribosomal RNA (rRNA) gene sequencing.[19] All isolates exhibited biochemical and 16S rRNA gene sequence features characteristic of Gram-positive eubacteria. After observation that several isolates appeared to self-organize in vitro, an isolate was selected which had features characteristic of the Gram-positive facultative anaerobe *Staphylococcus epidermidis* including a coccal morphology when observed in its unicellular form and the biochemical and 16S rRNA gene sequence profiles associated with *Staphylococcus epidermidis*. This isolate, designated as MH, was selected for further morphogenetic study.

EXAMPLE 3

Figure 2:
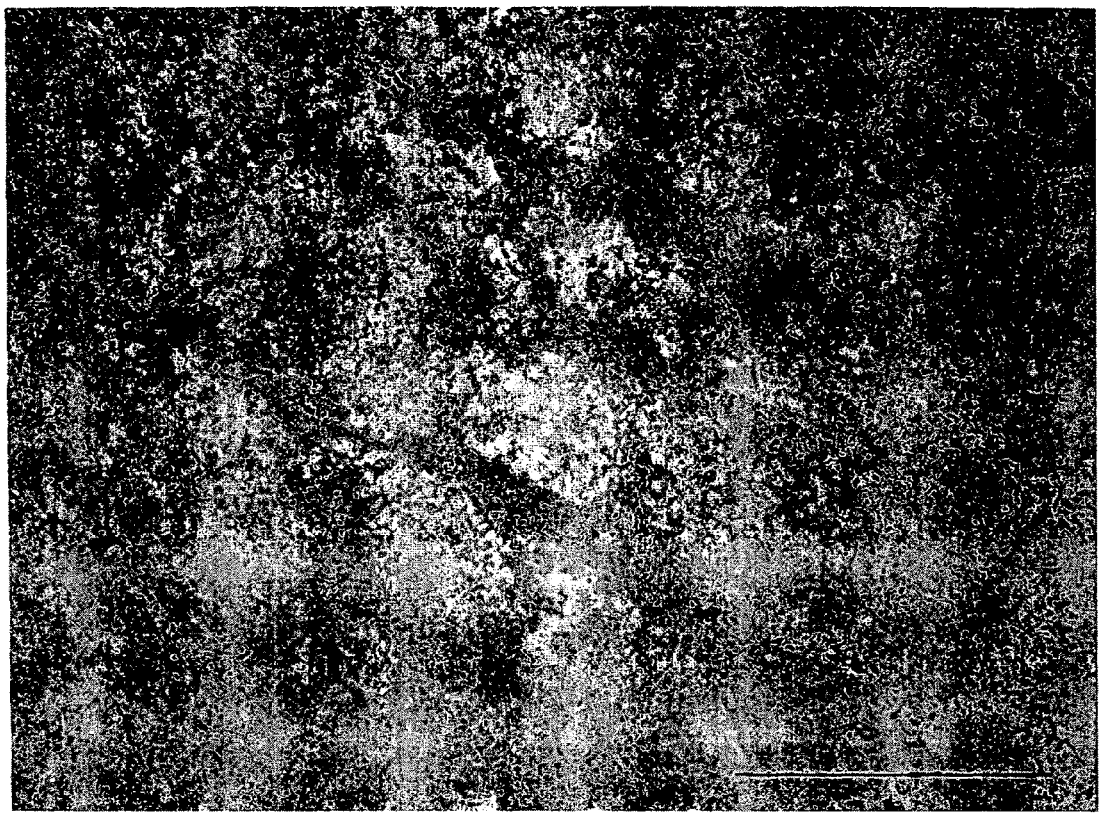
FIG. 2 shows the morphote isolate MH self-organized into reticular, honeycomb-like patterns under light microscopy (7-day old liquid culture; stained with the supravital dye new methylene blue N solution (Brecher formula) and examined by light microscopy). Scale bar=40 µm.
Figure 3:
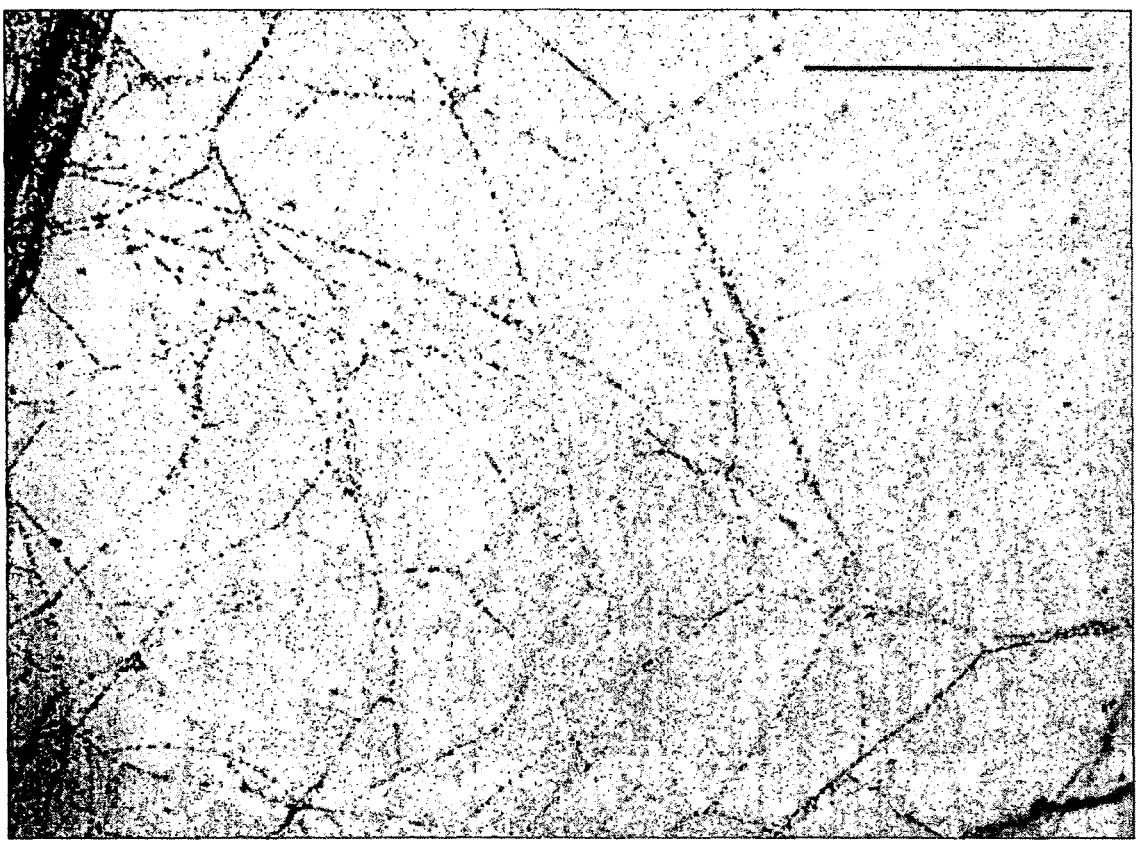
FIG. 3 shows the morphote isolate MH self-organized into a capillary-like network, under light microscopy. The edge of a multicellular tissue-like sheet appears in the upper left corner of this microphotograph (50-day old liquid culture; stained with the supravital dye new methylene blue N solution (Brecher formula) and examined by light microscopy). Scale bar=250 µm.

Within 72 hours of transfer from solid media into liquid culture, the isolate of Example 2 (MR) formed nonadherent, creamy-white, elastic material at the bottom of culture vessels. This property persisted despite repeated liquid-solid-liquid media transfers. After several more days in culture, microscopic examination of fresh culture preparations stained with the supravital dye new methylene blue N solution (Brecher formula) revealed tissue-like sheets that contained lacunae (FIG. 1). In some tissue-like sheets, reticular, honeycomb-like patterns were found in which the planar culture was tessellated with polygons with sides defined by cords of morphotes (FIG. 2). In addition, capillary-like networks composed of strands of morphotes were found attached to tissue-like sheets (FIG. 3) and floating free in the liquid medium. Morphote strands in capillary-like networks recoiled in turbulent medium, revealing their elastic properties.

Figure 4:
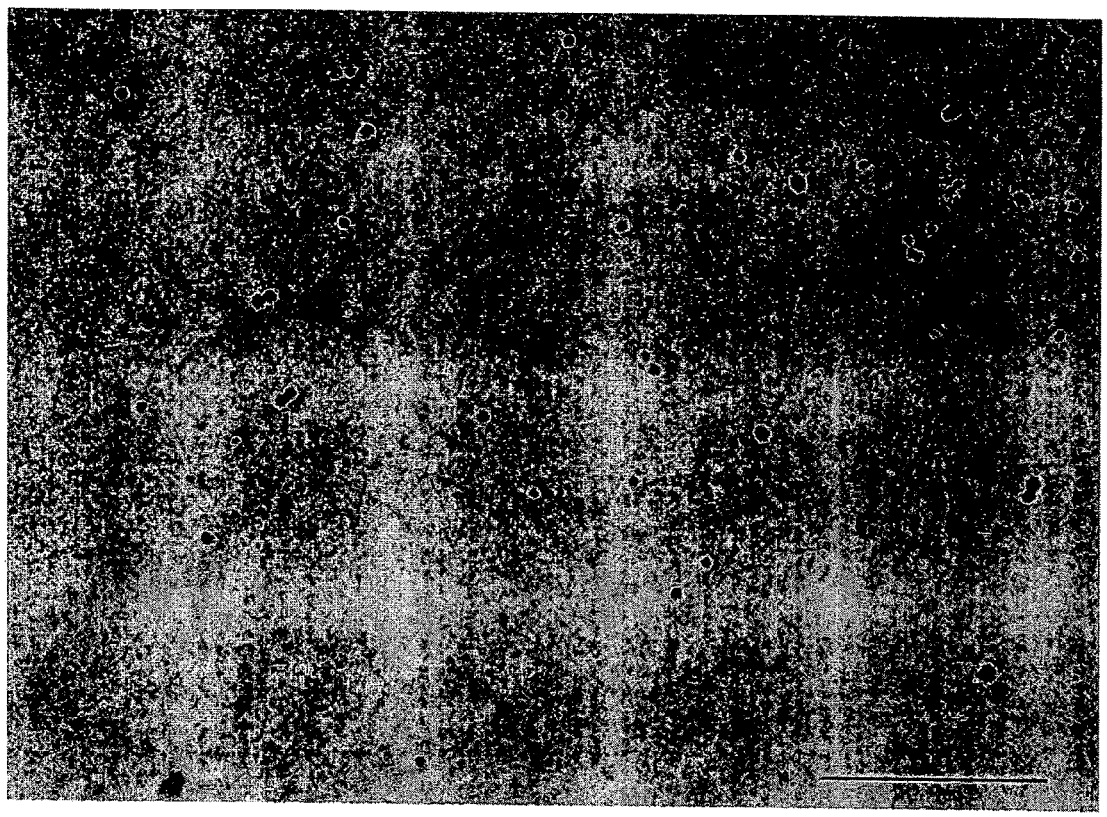
FIG. 4 MH self-organized into multicellular tissue-like sheets and capillary-like networks under light microscopy. In this black-and-white microphotograph, pleomorphic, cell wall-deficient bacteria appear gray while cocci with cell walls intact appear black (7-day old liquid culture). Scale bar=20 µm.
Figure 5:
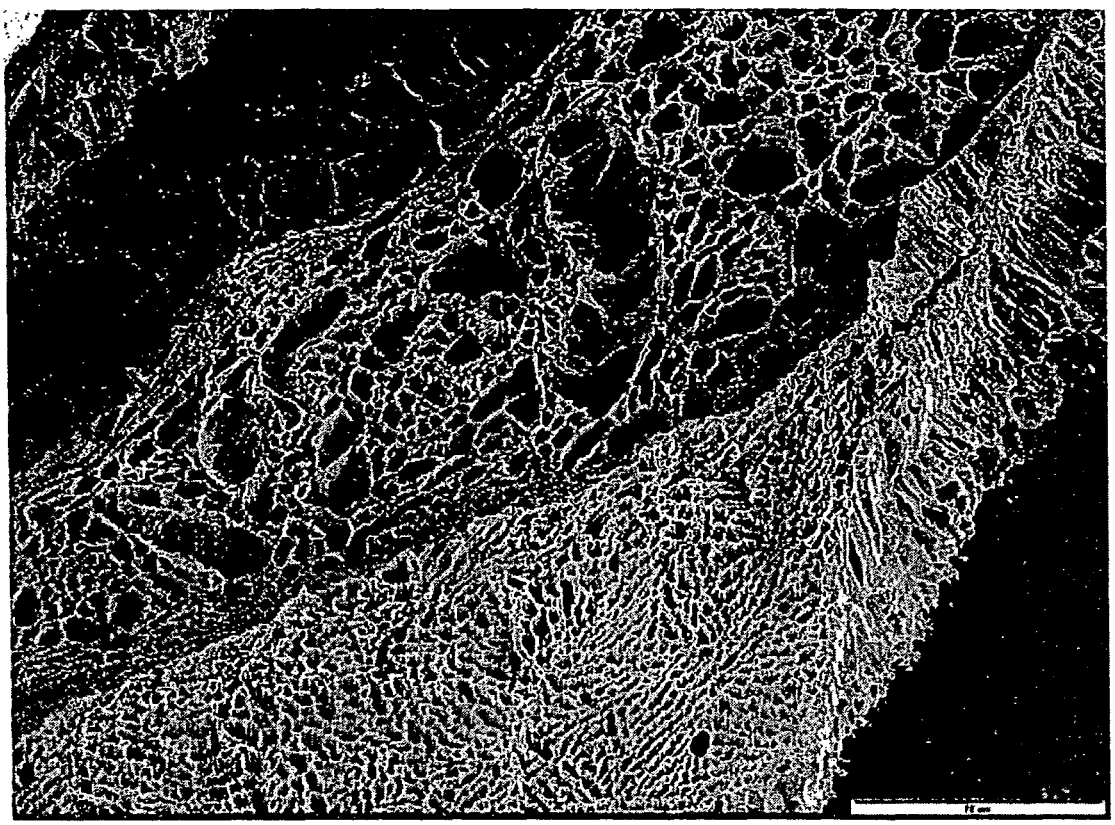
FIGS. 5-9 show the morphote isolate MH under scanning electron microscopy, which revealed self-organization into various multicellular tissue-level structures that resemble or are similar to honey comb, sponge, and mammalian trabecular bone. The depth of honeycomb-like structures can extend 30-40 µm or more. Scale bars are included in the right lower corner of each microphotograph.
Figure 6:
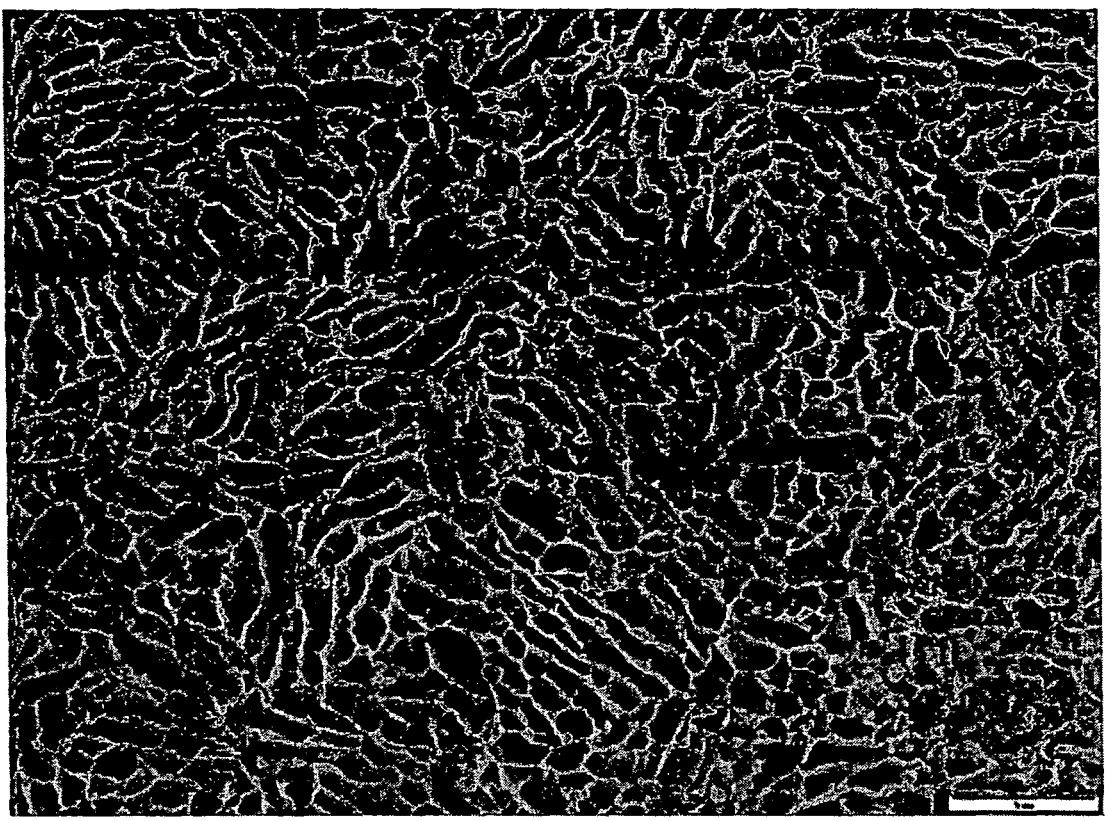
Figure 7:
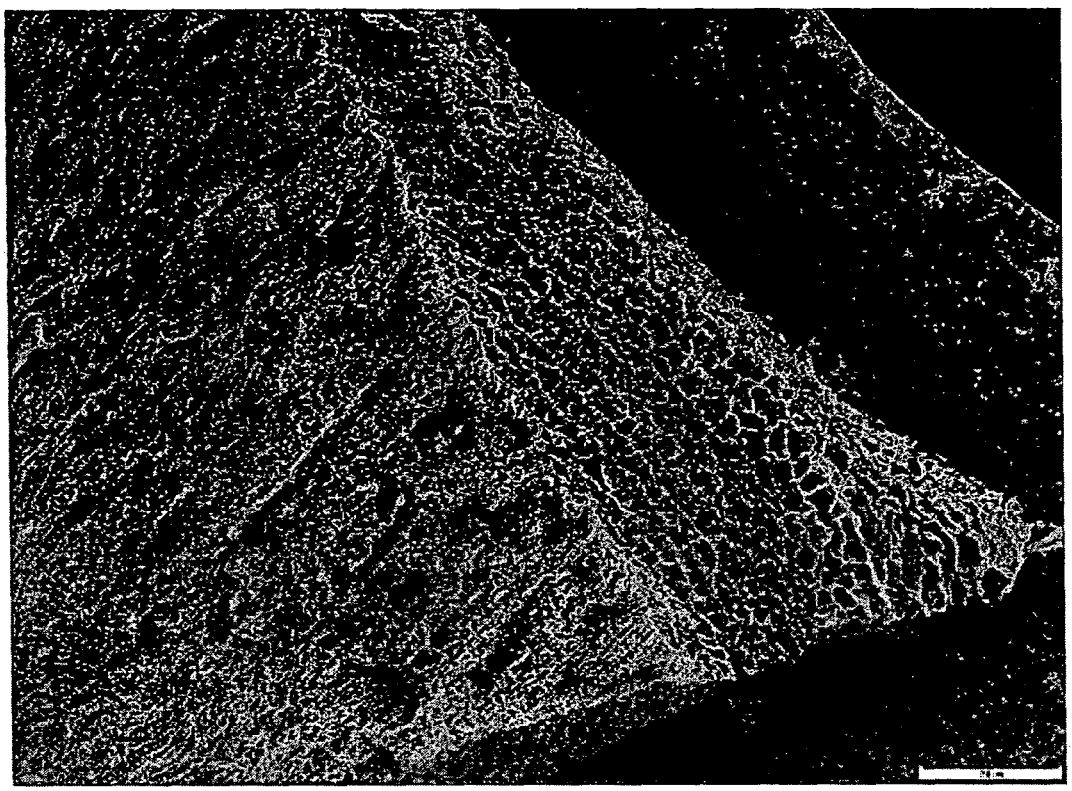
Figure 8:
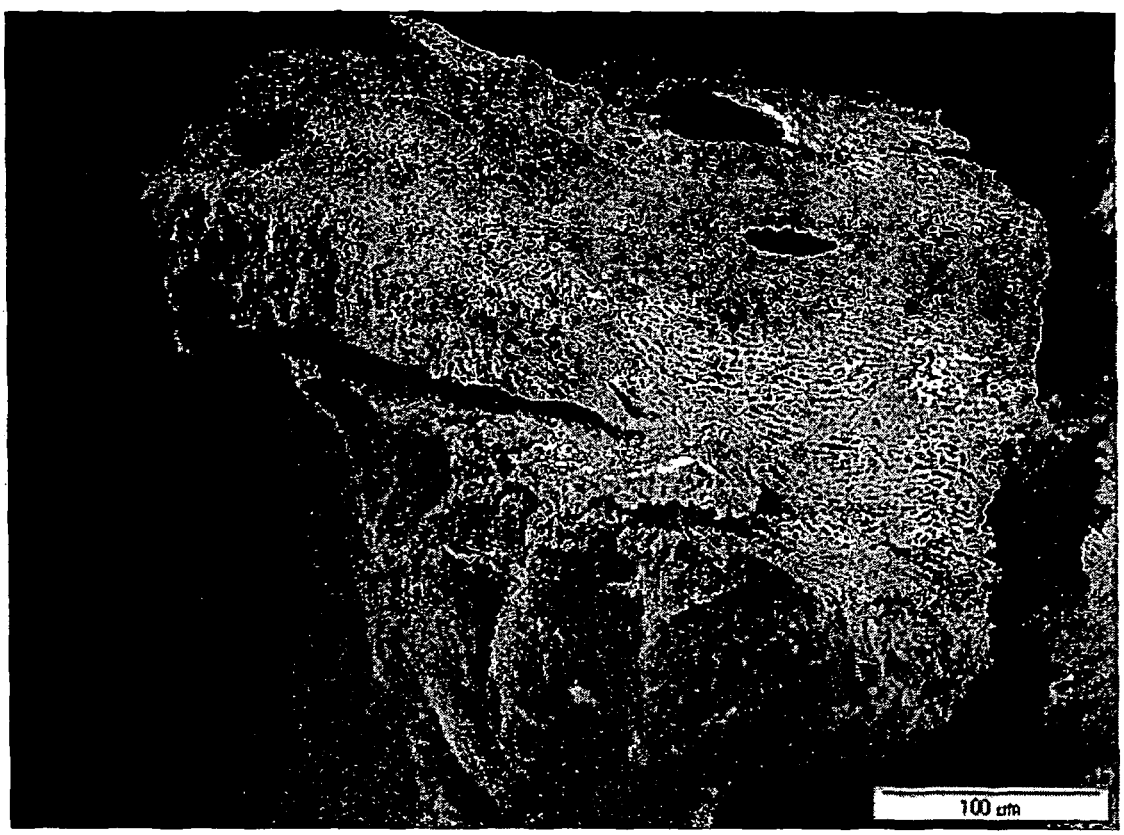
Figure 9:
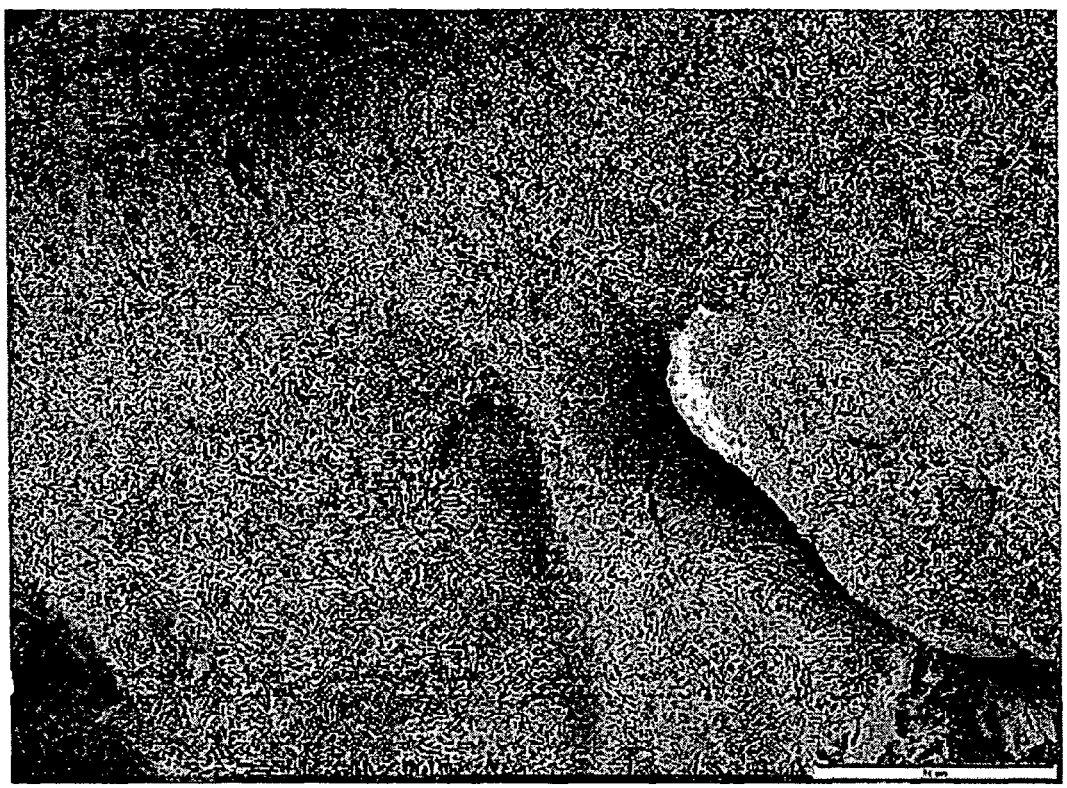

Microscopic examination of the Gram-stained tissue-like sheets at high magnification revealed a network of morphotes, many of which were Gram-negative by Gram-stain criteria (FIG. 4). Morphotes with a coccal (i.e., unicellular) morphology, single and in pairs, stained purple with the Gram stain procedure[20] and, consequently, exhibit eubacterial Gram-positive characteristics by Gram-stain criteria. These morphotes also exhibited biochemical and 16S ribosomal DNA sequence characteristics associated with Gram-positive eubacteria. Many of the morphotes comprising the multicellular networks stained red with the Gram stain procedure and, consequently, exhibited eubacterial Gram-negative characteristics by Gram-stain criteria, although they exhibited biochemical and 16S ribosomal DNA sequence characteristics associated with Gram-positive eubacteria. This finding suggests that their cell walls contain only small amounts of peptidoglycan.[20] The largest of these morphotes had undulating cell walls; the smallest appear as beads on a necklace and are a fraction of the size of a purple-stained coccus (~1 µm). Some triangular and quadrilateral areas circumscribed by this irregularly tessellated morphote network were 3-4 µm.[2] In fresh preparations, these bead-like morphote forms stained with the supravital dye new methylene blue N solution (Brecher formula) (liquid culture day 7). In the black-and-white microphotograph FIG. 4, pleomorphic, cell wall-deficient bacteria appear gray while cocci with cell walls intact appear black. If present in the tumor microenvironment, morphote networks of these dimensions would be difficult to detect using conventional histopathology techniques.

EXAMPLE 4

For scanning electron microscopy (SEM) studies of the isolate of Example 2 (MH), the isolate was cultivated in a total volume of 7 ml of tryptic soy broth (TSB) growth medium in sterile polystyrene culture tubes at 37° C. for 14 days without shaking; every third day, 2 ml of TSB were replaced with fresh TSB. Alternatively, the isolate was cultivated in 1.2 ml of TSB in each of 24 wells of a 24-well culture plate with Thermanox™ coverslips (Cat. No. 174950, Nunc, Rochester, N.Y., USA) placed on the bottom of each well; every second day, 1 ml of TSB in each well was replaced with fresh TSB.

Subsequently, 1 ml samples of the isolate in TSB were spotted on 1) Thermanox™ plastic coverslips or 2) SEM preparation stubs with carbon adhesive on which TEM grids were affixed and were frozen by quickly dipping samples in liquid propane. Alternatively, samples of the isolate cultivated on Thermanox™ coverslips in 24-well culture dishes were frozen by quickly dipping samples in liquid propane. Freeze substitution for all samples was performed in dry ethanol on dry ice in refrigeration so that samples gradually warmed to 4° C. Samples were then subjected to critical point drying, sputtercoated with 12 nm platinum, and examined by SEM. FIGS. 5-9. Examination by scanning electron microscopy revealed that the isolate of Example 2 self-organized into various multicellular tissue-level structures that resemble or are similar to honey comb, sponge, and mammalian trabecular bone. The depth of honeycomb-like structures can extend 30-40 µm or more. Scale bars are included in the right lower corner of each microphotograph.

EXAMPLE 5

For transmission electron microscopy (TEM) studies of the isolate of Example 2, the isolate was cultivated in 5 ml of growth medium for either 14 days or 12 weeks at 37° C. The isolate was fixed by carefully adding 5 ml of 5% glutaraldehyde with 1% ruthenium to each 5 ml culture of the isolate. The isolate in fixative was stored at 4° C. for 2 days.

Figure 10:
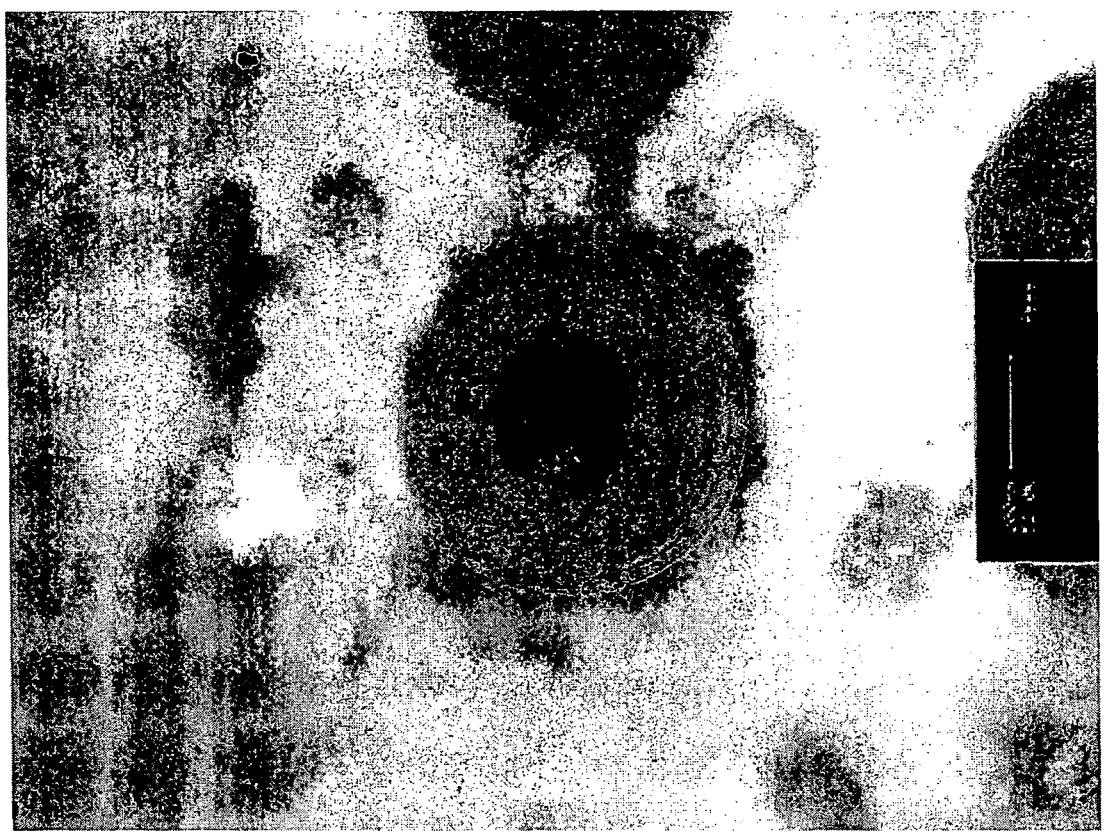
FIG. 10 shows the morphote isolate under transmission electron microscopy, which revealed the coccal unicellular morphology of the isolate. Scale bar, 200 nm.

Subsequently, the isolate in fixative was washed three times with sodium cacodylate buffer. Samples were then postfixed in 1% $OsO_4$ (osmium tertroxide) for 3 hours at room temperature and washed three times with sodium cacodylate buffer. Dehydration of samples was performed in a series of 70%, 90%, 96%, and 100% concentrations of ethanol, 20 minutes each step. Samples were infiltrated with a 1:1 mixture of 100% ethanol and LR White™ resin (LR White™ Resin System, London Resin Company Ltd., London, England, UK) for 20 minutes, followed by infiltration in pure LR White™ resin twice for 20 minutes each. Resin-infiltrated samples were polymerized at 60° C. for 12 hours, cut into 75 nm sections with a microtome, stained with 1% uranyl acetate, and examined by TEM. FIG. 10. Examination with transmission electron microscopy revealed the coccal unicellular morphology of the isolate of Example 2. The broad, dense cell wall observed (25-50 nm thick) is similar to the peptidoglycan-containing cell wall of various species of Gram-positive eubacteria. The darkly stained area in the center of the cell represents the nucleoid.

REFERENCES

1. Maynard Smith, J. & Szathmary, E. The Major Transitions in Evolution (Oxford University Press, Oxford/N.Y. 1995).
2. Velicer, G. J. & Yuen-tsu, N. Y. Nature 425, 75-78 (2003).
3. Murray J. D. C. R. Biol. 326, 239-252 (2003).
4. Serini G., et al. EMBO J. 22, 1771-1779 (2003).
5. Cartmell S., et al. J Biomed Mater Res A. 69, 97-104 (2004).
6. Wolschrijn C. F. & Weijs W. A. Anat. Rec. A Discov. Mol. Cell Evol. Biol. 278, 514-9 (2004).
7. Roufosse C. A., et al. Int J Biochem Cell Biol. 36, 585-97 (2004).
8. Tonini T., Rossi F. & Claudio P. P. Oncogene 22, 6549-6556 (2003).Murray J. D. C. R. Biol. 326, 239-252 (2003).
9. McFall-Ngai M. J. Dev. Biol. 242, 1-14 (2002).
10. Kempf V. A., Hitziger N., Riess T. & Autenrieth I. B. Trends Microbiol. 10, 269275 (2002).
11. Ullrich C. I. & Aloni R. J. Exp. Bot. 51, 951-1960 (2000).
12. Finch C. E. & Crimmins E. M. Science. 305, 1736-9 (2004).
13. Roubenoff R. Curr Opin Clin Nutr. Metab. Care. 6, 295-9 (2003).
14. Krabbe K. S., Pedersen M. & Bruunsgaard H. Exp. Gerontol. 39, 687-99 (2004).
15. Mavi G., et al. J. Trauma. 51, 728-35, (2001).
16. Seibert, F. B. et al. Ann. N. Y. Acad. Sci. 174, 690-728 (1970).
17. Koonin, E. V., Malkarova, K. S. & Aravind, L. Annu. Rev. Microbiol. 55, 709-742 (2001).
18. Robinson, D. H. U.S. Pat. No. 6,022,730 (2000).
19. Woo P. C. et al. J. Clin. Microbiol. 41, 1996-2001(2003).
20. Beveridge T. J. Biotech. Histochem. 76, 111-118 (2001).

I claim:

1. An in vitro culture of *Staphylococcus epidermidis* exhibiting a multicellular, mammalian tissue-like pattern.
2. The culture of claim 1 exhibiting sheet-like tissue-level multicellular self-organization.
3. The culture of claim 1 exhibiting capillary-like tissue-level multicellular self-organization.
4. The culture of claim 1 exhibiting trabecular (spongy) bone-like tissue-level multicellular self-organization.
5. The culture of claim 1, wherein three or more *Staphylococcus epidermidis* bacteria connect or interconnect into networks of varying densities, scales, or dimensions that tessellate triangular, quadrilateral, and polygonal areas or shapes that contain no morphote cells.

* * * * *